United States Patent
Kosak

(10) Patent No.: US 6,835,718 B2
(45) Date of Patent: Dec. 28, 2004

(54) BIOCLEAVABLE MICELLE COMPOSITIONS FOR USE AS DRUG CARRIERS

(75) Inventor: Kenneth M. Kosak, West Valley City, UT (US)

(73) Assignee: KK Biomed Corporation, Salt Lake City, UT (US)

( * ) Notice: Subject to any disclaimer, the term of this patent is extended or adjusted under 35 U.S.C. 154(b) by 184 days.

(21) Appl. No.: 09/829,551

(22) Filed: Apr. 10, 2001

(65) Prior Publication Data

US 2001/0021703 A1 Sep. 13, 2001

Related U.S. Application Data

(63) Continuation-in-part of application No. PCT/US99/30820, filed on Dec. 27, 1999, which is a continuation-in-part of application No. 09/223,055, filed on Dec. 30, 1998, now Pat. No. 6,048,736.

(51) Int. Cl.⁷ ...................... A01N 43/04; A61K 31/715; A61K 31/70; C08B 30/18; C08B 37/16
(52) U.S. Cl. ........................... 514/58; 514/44; 514/777; 514/778; 536/45; 536/46; 536/47; 536/55.3
(58) Field of Search ............................ 514/44, 58, 777, 514/778; 536/45, 46, 47, 55.3

(56) References Cited

U.S. PATENT DOCUMENTS

| 3,420,788 A | * | 1/1969 | Solms et al. |
| 4,727,064 A | * | 2/1988 | Pitha et al. |
| 5,068,227 A | * | 11/1991 | Weinshenker et al. |
| 5,558,857 A | * | 9/1996 | Klaveness et al. |
| 5,730,969 A | * | 3/1998 | Hora et al. |

* cited by examiner

Primary Examiner—James O. Wilson
Assistant Examiner—Traviss C. McIntosh, III

(57) ABSTRACT

This invention discloses compositions and methods for preparing biocleavable or biodegradable micelle compositions for carrying and releasing drugs and other active agents for therapeutic or other medical uses. Methods are also disclosed for preparing biocleavable cyclodextrin micelle carriers that release drugs under controlled conditions.

The invention also discloses biocleavable or biodegradable micelle compositions that are coupled to biorecognition molecules for targeting the delivery of drugs to their site of action.

10 Claims, No Drawings

BIOCLEAVABLE MICELLE COMPOSITIONS FOR USE AS DRUG CARRIERS

RELATED PATENT APPLICATIONS

This is a continuation-in-part of PCT/US99/30820, filed Dec. 27, 1999, which is a continuation-in-part of U.S. patent application Ser. No. 09/223,055, filed Dec. 30, 1998, now U.S. Pat. No. 6,048,736, issued Apr. 11, 2000. The contents of those applications are incorporated herein.

TECHNICAL FIELD OF THE INVENTION

This invention discloses methods for preparing biocleavable or biodegradable micelle compositions for carrying and releasing drugs and other active agents for therapeutic or other medical uses. Methods are also disclosed for preparing biocleavable cyclodextrin micelle carriers that release drugs under controlled conditions. The invention also discloses methods for preparing biocleavable micelle compositions that are coupled to biorecognition molecules for targeting the delivery of drugs to their site of action.

DESCRIPTION OF THE PRIOR ART

There is a need for carriers of drugs and active agents that facilitate their solubility, delivery and effectiveness. When drugs are bound to polymers of the prior art they can be taken up at the cell surface by endosomes (receptosomes) and transferred to the lysosomal compartment. This permits modulation of drug uptake through cell surface properties. Also, drug release can be controlled using specific enzymes and other conditions within the cell.

Drugs and other active agents delivered through micelle carriers have gained acceptance as a way for improving cancer chemotherapy and other drug therapies. Also, the prior art now employs drug-antibody or drug-polypeptide conjugates to re-direct anti-cancer and other agents to selected target cells.

Cyclodextrins and their derivatives have been shown to enhance the aqueous solubility of unmodified drugs and reduce the side effects in vivo. Soluble, individual cyclodextrin derivatives such as hydroxypropyl cyclodextrin (HPCD) disclosed by Pitha, U.S. Pat. Nos. 4,596,795 and 4,727,064 and sulfobutylether cyclodextrins (SBECD) disclosed by Stella, et al., U.S. Pat. Nos. 5,134,127 and 5,376,645 have been used as excipients for solubilizing drugs. The NIH currently holds a patent (U.S. Pat. No. 4,727,064) for the improvement of drug preparations using cyclodextrins. However, because individual cyclodextrins and even individual cyclodextrin derivatives easily dissociate from the drug with dilution, many of the advantages of cyclodextrins are limited with parenteral treatment.

The prior art of cyclodextrins has disclosed their use in labeling materials for in vitro testing (Kosak, PCT WO 91/05605, 1991), and in drug preparations (Hirai, et al, U.S. Pat. Nos. 4,523,031 and 4,523,037).

The preparation and use of individual cyclodextrins conjugated to biorecognition molecules as drug carriers is disclosed by Weinshenker, U.S. Pat. No. 5,068,227; 1991, where each coupling site is limited to one drug molecule. However, Weinshenker makes no disclosures or suggestions for any cyclodextrin polymers and they cannot be made with the synthesis methods disclosed. When drugs and other active agents as guest molecules are noncovalently bonded to the individual cyclodextrins of the prior art, they are subject to excessive dissociation, which results in uncontrolled release of drug even before the carriers reach their targets.

Review articles on the pharmaceutical applications of cyclodextrins have identified many problems due to the high turnover rate between inclusion complex formation and dissociation. Stella, V. J., et al., Pharmaccut. Res. 14, 556–567 (1997), report that even with the strongest theoretical binding constants, as soon as the complex of free cyclodextrin and drug is diluted in the bloodstream, over 30% is calculated to dissociate. Also, Rajewski, R., et al, J. Pharm. Sci. 85, 1142–1169(1996), solubilized the anti-cancer drug Taxol™ with cyclodextrins. They reported on page 1145 that "any attempt to dilute the samples resulted in erratic precipitation" due to competitive displacement factors found in plasma. Because of these problems, cyclodextrins in the prior art are used for solubilizing and stabilizing certain drugs before or during administration but are not suitable for carrying and delivering drugs in the bloodstream. The cyclodextrin micelle carriers of the instant invention overcome these problems and provide the new function of controlled release, which is not disclosed or suggested by the prior art.

SUMMARY DISCLOSURE OF THE INVENTION

Micelle Polymer Carriers with Controlled Release

A micelle polymer carrier is a new invention defined herein as a water-soluble (or colloidal) micelle that has been suitably polymerized so that it completely entraps a drug or other active agent within. The formation of micelles for carrying drugs is well known. However, micelle carriers of the prior art suffer from uncontrolled loss of the drug due to diffusion. This invention solves that problem through cross-linking the micelle components to completely entrap the drug until it is delivered to the site of action.

For this invention, any suitable synthesis method now used for preparing drug-carrying micelles, with suitable modification, is applicable to the synthesis of this invention including the disclosures of G. S. Kwon, IN: Critical Reviews in Therapeutic drug Carrier Systems, 15(5):481–512 (1998), and references therein. A distinguishing property of this invention is that the micelle-forming components must have suitable functional groups or biocleavable moieties available on their hydrophilic "heads" to permit cross-linking after the micelle has been formed with a drug inside.

In one preferred embodiment, suitable micelles are formed that contain a drug. Then the hydrophilic head groups are suitably cross-linked using various bifunctional cross-linking agents so that the micelle cannot release the entrapped drug. The preferred embodiment has incorporated cross-links that contain biocleavable linkages as described herein. In another embodiment, the biocleavable micelle includes cyclodextrins or cyclodextrin dimers, trimers or polymers. Also, these micelle carriers can be suitably targeted by coupling suitable biorecognition molecules to the surface.

It has been discovered that the biocleavable micelle of the instant invention overcome the problems of other micelles in the prior art. The instant invention provides new properties and unexpected advantages. In its simplest form, a biocleavable micelle comprises a micelle that has a drug or other active agent completely entrapped within it.

In one embodiment, the biocleavable micelles of the instant invention, by complete entrapment of the active agent, solve the problem of losing drug or other active agent by diffusion when diluted in vivo. In another embodiment, the invention also provides a means for controlled release of the entrapped drug in vivo, which was not possible in the prior art of micelles.

In another embodiment, the invention also provides a means for targeting the biocleavable micelle carrier by coupling it to a biorecognition molecule.

INDUSTRIAL APPLICABILITY.

These biocleavable micelle carriers can be used in many fields of medicine to deliver therapeutic drugs and other agents through a variety of routes including orally, nasally and parenterally. Other routes include various applications for delivery through ocular membranes and mucosal membranes, including the use of electric charge as in iontophoresis. They can also be used to deliver nucleic acids such as oligonucleotides to treat various diseases by these routes.

DESCRIPTION OF THE BEST MODES FOR CARRYING OUT THE INVENTION

For the purposes of disclosing this invention, certain words, phrases and terms used herein are defined as follows:

Active Agents.

Active agents function as the preferred guest molecules of the instant invention. Active agents that are preferred in the instant invention are chemicals and other substances that can be entrapped within a micelle or form an inclusion complex with a cyclodextrin and are inhibitory, antimetabolic, therapeutic or preventive toward any disease (i.e. cancer, syphilis, gonorrhea, influenza and heart disease) or inhibitory or toxic toward any disease causing agent. Preferred active agents are any therapeutic drugs categorized in The Merck Index, Eleventh Ed., Merck & Co. Inc., Rahway N.J. (1989) and those listed by Cserhati, T., Anal.Biochem. 225(2), 328–332 (1995).

Active agents include but are not limited to therapeutic drugs that include prodrugs, anticancer drugs, antineoplastic drugs, antifungal drugs, antibacterial drugs, antiviral drugs, cardiac drugs, neurological drugs, and drugs of abuse; alkaloids, antibiotics, bioactive peptides, steroids, steroid hormones, polypeptide hormones, interferons, interleukins, narcotics, nucleic acids including antisense oligonucleotides, pesticides and prostaglandins.

Active agents also include any toxins including aflatoxins, ricins, bungarotoxins, irinotecan, ganciclovir, furosemide, indomethacin, chlorpromazine, methotrexate, cevine derivatives and analogs including cevadines, desatrines, and veratridine, among others.

Active agents also included but are not limited to, are;
various flavone derivatives and analogs including dihydroxyflavones (chrysins), trihydroxyflavones (apigenins), pentahydroxyflavones (morins), hexahydroxyflavones (myricetins), flavyliums, quercetins, fisetins;
various antibiotics including derivatives and analogs such as penicillin derivatives (i.e. ampicillin), anthracyclines (i.e. doxorubicin, daunorubicin, mitoxantrone), butoconazole, camptothecin, chalcomycin, chartreusin, chrysomicins (V and M), chloramphenicol, chlorotetracyclines, clomocyclines, cyclosporins, ellipticines, filipins, fungichromins, griseofulvin, griseoviridin, guamecyclines, macrolides (i.e. amphotericins, chlorothricin), methicillins, nystatins, chrymutasins, elsamicin, gilvocarin, ravidomycin, lankacidin-group antibiotics (i.e. lankamycin), mitomycin, teramycins, tetracyclines, wortmannins;
various anti-microbials including reserpine, spironolactone, sulfacetamide sodium, sulphonamide, thiamphenicols, thiolutins;
various purine and pyrimidine derivatives and analogs including 5'-fluorouracil 5'-fluoro-2'-deoxyuridine, and allopurinol;
various photosensitizer substances, especially those used for singlet and triplet oxygen formation useful for photodynamic therapy (van Lier, J. E. In "Photodynamic Therapy of Neoplastic Disease"; Kessel, D., Ed., CRC Press, Boca Raton, FL, 1990, Vol. 1), including meso-chlorin e6 monoethylenediamine ($Mce_6$), phytalocyanine, porphyrins and their derivatives and analogs;
various steroidal compounds such as cortisones, estradiols, hydrocortisone, testosterones, prednisolones, progesterones, dexamethasones, beclomethasones and other methasone derivatives, other steroid derivatives and analogs including cholesterols, digitoxins, digoxins, digoxigenins;
various coumarin derivatives and analogs including dihydroxycoumarins (esculetins), dicumarols, chrysarobins, chrysophanic acids, emodins, secalonic acids;
various dopas, derivatives and analogs including dopas, dopamines, epinephrines, and norepinephrines (arterenols);
various antineoplastic agents or cell growth inhibitors such as cisplatins and taxanes including paclitaxel and docetaxel;
various barbiturates including phenobarbitone, amobarbital, allobarbital, pentobarbital and other barbital derivatives;
various benzene derivatives including amino-benzoic acid, bromobenzoic acid, benzocaine, benzodiazepines, benzothiazide, butyl-p-aminobenzoate;
various polypeptide derivatives;
various carboxylic acid derivatives such as bromoisovalerylurea, phenyl-butyric acid, phenylvaleric acid;

Other active agents include, but are not limited to, diphenyl hydantoin, adiphenine, anethole, aspirin, azopropazone, bencyclane, chloralhydrate, chlorambucil, chlorpromazine, chlorogenin, cinnamic acid, clofibrate, coenzyme A, cyclohexyl anthranilate, diazepam, flufenamic acid, fluocinolone acetonide, flurbiprofen, guaiazulene, ibuprofen, indican, indomethacin, iodine, ketoprofen, mefanamic acid, menadione, metronidazole, nitrazepam, phenytoin, propylparaben, proscillaridin, quinolone, thalidomide, thiamine dilaurylsulphate, thiopental, triamcinolone, vitamins A, D3, E, K3, and warfarin.

Other specific active agents are anti-viral drugs, nucleic acids and other anti-viral substances including those against any DNA and RNA viruses, AIDS, HIV and hepatitis viruses, adenoviruses, alphaviruses, arenaviruses, coronaviruses, flaviviruses, herpesviruses, myxoviruses, oncornaviruses, papovaviruses, paramyxoviruses, parvoviruses, picomaviruses, poxviruses, reoviruses, thabdoviruses, rhinoviruses, togaviruses and viriods; any anti-bacterial drugs, nucleic acids and other anti-bacterial substances including those against gram-negative and gram-positive bacteria, acinetobactet, achromobacter, bacteroides, clostridium, chlamydia, enterobacteria, haemophilus, lactobacillus, neisseria, staphyloccus, and streptoccocus; any antifungal drugs, nucleic acids and other anti-fungal substances including those against aspergillus, candida, coccidiodes, mycoses, phycomycetes, and yeasts; any drugs, nucleic acids and other substances against mycoplasma and rickettsia; any anti-protozoan drugs, nucleic acids and other substances; any anti-parasitic drugs, nucleic acids and other substances; any drugs, nucleic acids and other substances against heart diseases, tumors, and virus infected cells, among others.

Nucleic Acid Active Agents.

For the purposes of this invention, certain nucleic acids are preferred as active agents against viral and other microbial diseases, against cancers, autoimmune and genetic diseases. They also include specific DNA sequences used for gene therapy. Nucleic acid active agents include all types of RNA, all types of DNA, and oligonucleotides including probes and primers used in the polymerase chain reaction (PCR), hybridizations or DNA sequencing. Also preferred are phosphodiester antisense oligonucleotides, antisense oligodeoxynucleotides (ODN) and any oligonucleotides or oligodeoxynucleotides where the sugar-phosphate "backbone" has been derivatized or replaced with "backbone analogues" such as with phosphorothioate, phosphorodithioate, phosphoroamidate, alkyl phosphotriester, or methylphosphonate linkages or "backbone analogues". Also preferred are antisense oligonucleotides, antisense ODN and any oligonucleotides or oligodeoxynucleotides with non-phosphorous backbone analogues such as sulfamate, 3'-thioformacetal, methylene (methylimino) (MMI), 3'-N-carbamate, or morpholino carbamate.

Some preferred examples of synthetic oligonucleotides and ODNs are disclosed by J. F. Milligan, et al., J. Medicinal Chem. 36(14): 1923–1937 (1993) and Y. Shoji, et al., Antimicrob. Agents Chemotherapy, 40(7):1670–1675 (1996). Also included are synthetic nucleic acid polymers and peptide nucleic acids (PNA) disclosed by Egholm, et al, Nature 365:566–568(1993) and references therein, including PNA clamps (Nucleic Acids Res. 23:217(1995)). Also included are nucleotide mimics or co-oligomers like phosphoric acid ester nucleic acids (PHONA), disclosed by Peyman, et aL, Angew. Chem. Int. Ed. EngL 36:2809–2812 (1997). Also included are DNA and/or RNA fragments, and derivatives from any tissue, cells, nuclei, chromosomes, cytoplasm, mitochondria, ribosomes, and other cellular sources.

Biocleavable Linkage or Bond.

For the instant invention, biocleavable linkages are defined as types of specific chemical moieties or groups used within the chemical substances that covalently or non-covalently couple and cross-link the biocleavable micelle or biocleavable cyclodextrin micelle carriers. They are contained in certain embodiments of the instant invention that provide the function of controlled release of an entrapped drug or other active agent. Biocleavable linkages or bonds are distinguishable by their structure and function and are defined here under distinct categories or types.

One category comprises the disulfide linkages that are well known for covalently coupling drugs to polymers. For drug delivery, they may be more useful for shorter periods in vivo since they are cleaved in the bloodstream relatively easily. The simple ester bond is another type that includes those between any acid and alcohol. Another type is any imidoester formed from alkyl imidates. Also included are maleimide bonds as with sulfhydryls or amines used to incorporate a biocleavable linkage.

Another category comprises linkages or bonds that are more specifically cleaved after entering the cell (intracellular cleavage). The preferred linkages for release of drugs within the cell are cleavable in acidic conditions like those found in lysosomes. One type is an acidsensitive (or acid-labile) hydrazone linkage as described by Greenfield, et al, Cancer Res. 50, 6600–6607 (1990), and references therein. Another type of preferred acid-labile linkage is any type of polyortho or diortho ester linkage, examples disclosed by J. Heller, et al., Methods in Enzymology 112, 422–436 (1985), J. Heller, J. Adv. Polymer Sci. 107, 41 (1993), M. Ahmad, et al., J. Amer. Chem. Soc. 101, 2669(1979) and references therein.

Another preferred category of biocleavable linkages is biocleavable polypeptides preferably from 2 to 100 residues in length. These are defined as certain natural or synthetic polypeptides that contain certain amino acid sequences (i.e. are usually hydrophobic) that are cleaved by specific enzymes such as cathepsins, found primarily inside the cell (intracellular enzymes). Using the convention of starting with the amino or "N" terminus on the left and the carboxyl or "C" terminus on the right, some examples are: any polypeptides that contain the sequence Phe-Leu, Leu-Phe or Phe-Phe, such as Gly-Phe-Leu-Gly, Gly-Phe-Leu-Phe-Gly and Gly-PhePhe-Gly, and others that have either of the Gly residues substituted for one or more other peptides. Also included are leucine enkephalin derivatives such as Tyr-Gly-Gly-Phe-Leu.

Another preferred type of biocleavable linkage is any "hindered" or "protected" disulfide bond that sterically inhibits attack from thiolate ions. Examples of such protected disulfide bonds are found in the coupling agents: S-4-succinimidyl-oxycarbonyl-ø-methyl benzyl thiosulfate (SMBT) and 4-succinimidyloxycarbonyl-ø-methyl-ø-(2-pytidyldithio) toluene (SMPT). Another useful coupling agent resistant to reduction is SPDB disclosed by Worrell, et al., Anticancer Drug Design 1:179–188 (1986). Also included are certain aryldithio thiomidates, substituted with a methyl or phenyl group adjacent to the disulfide, which include ethyl S-acetyl 3-mercaptobutyrothioimidate (M-AMPT) and 3-(4-carboxyamidophenyldithio) proprionthioimidate (CDPT), disclosed by S. Arpicco, et al., Bioconj. Chem. 8 (3):327–337 (1997). Another preferred category is certain linkages or bonds subject to hydrolysis that include various aldehyde bonds with amino or sulfhydryl groups. Also included are N-hydroxysuccinimide or NHS bonds as with sulfhydryls or amines.

Another preferred type of biocleavable linkage is any suitable aromatic azo linkages that are cleavable by specific azo reductase activities in the colon as disclosed by J. Kopecek, et al., In: Oral Colon Specific Drug Delivery; D. R. Friend, Ed., pp 189–211 (1992), CRC Press, Boca Raton, Fla.

Biorecognition Molecules.

For the purposes of this invention, biorecognition molecules are those that bind to a specific biological substance or site. The biological substance or site is considered the "target" of the biorecognition molecule that binds to it. In the prior art, many drugs are "targeted" by coupling them to a biorecognition molecule that has a specific binding affinity for the cells, tissue or organism that the drug is intended for. For targeting a drug or other active agent in this invention, a biorecognition molecule is coupled to a biocleavable micelle or biocleavable CDM carrier that has the drug or active agent entrapped within. Examples of biorecognition molecules are described below.

Ligand.

A ligand functions as a type of biorecognition molecule defined as a selectively bindable material that has a selective (or specific), affinity for another substance. The ligand is recognized and bound by a usually, but not necessarily, larger specific binding body or "binding partner", or "receptor". Examples of ligands suitable for targeting are antigens, haptens, biotin, biotin derivatives, lectins, galactosamine and fucosylamine moieties, receptors, substrates, coenzymes and cofactors among others.

When applied to the biocleavable micelle or biocleavable CDMs of this invention, a ligand includes an antigen or hapten that is capable of being bound by, or to, its corresponding antibody or fraction thereof Also included are viral antigens or hemagglutinins and neuraminidases and nucleocapsids including those from any DNA and RNA viruses, AIDS, HIV and hepatitis viruses, adenoviruses, alphaviruses, arenaviruses, coronaviruses, flaviviruses, herpesviruses, myxoviruses, oncornaviruses, papovaviruses, paramyxoviruses, parvoviruses, picornaviruses, poxviruses, reoviruses, rhabdoviruses, rhinoviruses, togaviruses and viroids; any bacterial antigens including those of gram-negative and gram-positive bacteria, acinetobacter, achromobacter, bacteroides, clostridium, chlamydia, enterobacteria, haemophilus, lactobacillus, neisseria, staphyloccus, and streptoccocus; any fingal antigens including those of aspergillus, candida, coccidiodes, mycoses, phycomycetes, and yeasts; any mycoplasma antigens; any rickettsial antigens; any protozoan antigens; any parasite antigens; any human antigens including those of blood cells, virus infected cells, genetic markers, heart diseases, oncoproteins, plasma proteins, complement factors, rheumatoid factors. Included are cancer and tumor antigens such as alpha-fetoproteins, prostate specific antigen (PSA) and CEA, cancer markers and oncoproteins, among others.

Other substances that can function as ligands for biorecognition are certain vitamins (i.e. folic acid, $B_{12}$), steroids, prostaglandins, carbohydrates, lipids, antibiotics, drugs, digoxins, pesticides, narcotics, neuro-transmitters, and substances used or modified such that they function as ligands. Most preferred are certain proteins or protein fragments (i.e. hormones, toxins), and synthetic or natural polypeptides with cell affinity. Ligands also include various substances with selective affinity for ligators that are produced through recombinant DNA, genetic and molecular engineering. Except when stated otherwise, ligands of the instant invention also include the ligands as defined by K. E. Rubenstein, et al, U.S. Pat. No. 3,817,837 (1974).

Ligator.

A ligator functions as a type of biorecognition molecule defined for this invention as a specific binding body or "partner" or "receptor", that is usually, but not necessarily, larger than the ligand it can bind to. For the purposes of this invention, it is a specific substance or material or chemical or "reactant" that is capable of selective affinity binding with a specific ligand. A ligator can be a protein such as an antibody, a nonprotein binding body or a "specific reactor."

When applied to this invention, a ligator includes an antibody, which is defined to include all classes of antibodies, monoclonal antibodies, chimeric antibodies, Fab fractions, fragments and derivatives thereof Under certain conditions, the instant invention is also applicable to using other substances as ligators. For instance, other ligators suitable for targeting include naturally occurring receptors, any hemagglutinins and cell membrane and nuclear derivatives that bind specifically to hormones, vitamins, drugs, antibiotics, cancer markers, genetic markers, viruses, and histocompatibility markers. Another group of ligators includes any RNA and DNA binding substances such as polyethylenimine (PEI) and polypeptides or proteins such as histones and protamines.

Other ligators also include enzymes, especially cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, ribosomes, bacteriophages, cytochromes, lectins, certain resins, and organic polymers.

Preferred biorecognition molecules also include various substances such as any proteins, protein fragments or polypeptides with affinity for the surface of any cells, tissues or microorganisms that are produced through recombinant DNA, genetic and molecular engineering. For instance, any suitable membrane transfer proteins such as TAT, from HIV virus.

Cyclodextrin.

A cyclodextrin (CD), is an oligosaccharide composed of glucose monomers coupled together to form a conical, hollow molecule with a hydrophobic interior or cavity. The cyclodextrins of the instant invention can be any suitable cyclodextrin, including alpha-, beta-, and gamma-cyclodextrins, and their combinations, analogs, isomers, and derivatives. They function as components in the synthesis of the biocleavable micelle or biocleavable CDM carriers of the instant invention.

In describing this invention, references to a cyclodextrin "complex", means a noncovalent inclusion complex. An inclusion complex is defined herein as a cyclodextrin functioning as a "host" molecule, combined with one or more "guest" molecules that are contained or bound, wholly or partially, within the hydrophobic cavity of the cyclodextrin or its derivative.

Most preferred are cyclodextrin dimers, trimers and polymers containing cyclodextrin derivatives such as carboxymethyl CD, glucosyl CD, maltosyl CD, hydroxypropyl cyclodextrins (HPCD), 2-hydroxypropyl cyclodextrins, 2,3-dihydroxypropyl cyclodextrins (DHPCD), sulfobutylether cyclodextrins (SBECD), ethylated and methylated cyclodextrins.

Also preferred are oxidized cyclodextrins that provide aldehydes and any oxidized forms of any cyclodextrin polymers or derivatives that provide aldehydes. Some examples of suitable derivatives are disclosed by Pitha, J., et al, J. Pharm. Sci. 75, 165–167 (1986) and Pitha, J., et al, Int. J. Pharmaceut. 29, 73–82 (1986).

Also preferred are any amphiphilic CD derivatives such as those disclosed by Y. Kawabata, et al.,Chem. Lett. p1933 (1986), K. Chmurski, et al., Langmuir 12, 4046 (1996), P. Zhang, et al., Tetr. Lett. 32, No0.24, 2769(1991), P. Zhang, et al., J. Phys. Org. Chem. 5, 518 (1992), M. Tanaka, et al., Chem. Lett. p1307 (1987), S. Taneva, et al., Langmuir 5, 111 (1989), M. Weisser, et al., J. Phys. Chem. 100, 17893 (1996), L. A. Godinez, et al., Langmuir 14, 137 (1998) and D. Duchene, "International Pharmaceut. Applic. of Cyclodextrins Conference", Lawrence, Kans., USA, June 1997.

Also included are altered forms, such as crown ether-like compounds prepared by Kandra, L., et al, J. Inclus. Phenom. 2, 869–875 (1984), and higher homologues of cyclodextrins, such as those prepared by Pulley, et al, Biochem. Biophys. Res. Comm. 5, 11 (1961). Some useful reviews on cyclodextrins are: Atwood J.E.D., et al, Eds., "Inclusion Compounds", vols. 2 & 3, Academic Press, NY (1984); Bender, M. L., et al, "Cyclodextrin Chemistry", Springer-Verlag, Berlin, (1978) and Szejtli, J., "Cyclodextrins and Their Inclusion Complexes", Akademiai Kiado, Budapest, Hungary (1982). These references, including references contained therein, are applicable to the synthesis of the preparations and components of the instant invention and are hereby incorporated herein by reference.

Cyclodextrin Dimers, Trimers and Polymers.

For this invention, individual cyclodextrin derivatives (CD-monomer) function as one of the primary structures, or components, or units used to synthesize cyclodextrin micelle carriers. Also, certain CD dimers, and trimers can be used as units to synthesize cyclodextrin micelle carriers. In order to be used in CD micelle carriers they preferably have been derivatized to provide amphiphilic properties, or they are incorporated into an amphiphilic molecule.

A cyclodextrin dimer is a specific type of cyclodextrin derivative defined as two cyclodextrin molecules covalently coupled or cross-linked together to enable cooperative complexing with a guest molecule. Examples of some CD dimers that can be derivatized and used in the drug carriers of this invention, are described by; Breslow, R., et al. Amer. Chem. Soc. 111, 8296–8297 (1989); Breslow, R., et al, Amer. Chem. Soc. 105, 1390 (1983) and Fujita, K, et al, J. Chem. Soc., Chem. Commun., 1277 (1984).

A cyclodextrin trimer is a specific type of cyclodextrin derivative defined as three cyclodextrin molecules covalently coupled or cross-linked together to enable cooperative complexing with a guest molecule. A cyclodextrin polymer is defined as a unit of more than three cyclodextrin molecules covalently coupled or cross-linked together to enable cooperative complexing with several guest molecules.

A CD-block is defined as a CD dimer, trimer or polymer that is used as the primary component, or unit (i.e. building block) for additional crosslinking with other CD dimers, trimers or polymers to synthesize a CD polymer carrier. Generally this involves at least two steps. First the CD-blocks are prepared by crosslinking CD monomers and derivatizing to provide amphiphilic properties. Then the CD-blocks are incorporated into a micelle and crosslinked to entrap the active agent in the final CD micelle carrier composition.

For this invention, preferred cyclodextrin dimer, trimer and polymer units are synthesized by covalently coupling through chemical groups such as through coupling agents. The synthesis of preferred cyclodextrin dimer, trimer and polymer units does not include the use of proteins or other "intermediate coupling substances" (defined below), which can be incorporated during final synthesis of the biocleavable micelle or biocleavable cyclodextrin micelle carrier. Cooperative complexing means that in situations where the guest molecule is large enough, the member cyclodextrins of the CD dimer, trimer or polymer can each noncovalently complex with different parts of the same guest molecule, or with smaller guests, alternately complex with the same guest.

The prior art has disclosed dimers and polymers comprised of cyclodextrins of the same size. An improved cyclodextrin dimer, trimer or polymer comprises combinations of different sized cyclodextrins to synthesize these units. These combinations may more effectively complex with guest molecules that have heterogeneous complexing sites. Combinations for this invention can include the covalent coupling of an alpha CD with a beta CD, an alpha CD with a gamma CD, a beta CD with a gamma CD and polymers with various ratios of alpha, beta and gamma cyclodextrins.

Micelle.

A micelle is defined as a water soluble or colloidal structure or aggregate (also called a nanosphere or nanoparticle) composed of one or more amphiphilic molecules. The micelles of this invention have a single, central and primarily hydrophobic zone or "core" surrounded by a hydrophilic layer or "shell". Micelles range in size from 5 to about 2000 nanometers, preferably from 10 to 400 nm. Micelles of this invention are distinguished from and exclude liposomes which are composed of bilayers.

Amphiphilic molecules are those that contain at least one hydrophilic (polar) moiety and at least one hydrophobic (nonpolar) moiety. The micelles of this invention can be composed of either a single monomolecular polymer containing hydrophobic and hydrophilic moieties or an aggregate mixture containing many amphiphilic (i.e. surfactant) molecules formed at or above the critical micelle concentration (CMC), in a polar (i.e. aqueous) solution. The micelle is self-assembled from one or more amphiphilic molecules where the moieties are oriented to provide a primarily hydrophobic interior core and a primarily hydrophilic exterior.

Biocleavable Micelle Carrier.

A biocleavable micelle carrier is a new micelle composition provided by the instant invention. It is defined as a micelle containing a completely entrapped active agent with biodegradable or biocleavable linkages between the hydrophilic moieties of the micelle. The biocleavable crosslinks stabilize the micelle to prevent any significant amount of active agent from dissociating from the micelle. A biocleavable micelle carrier also provides the function or property of controlled release where the active agent is released upon lysis or cleavage of the biocleavable linkages. The most preferred compositions are stable under physiological conditions such as in the bloodstream, but are biodegraded to release active agent when in contact with certain organs or tissues or when taken into certain cells or microorganisms.

In a preferred embodiment the capturing is accomplished through complete physical entrapment by the micelle carrier. In this embodiment, "completely entrapped" means that the active agent is not covalently coupled to the micelle but is physically entrapped by the covalently cross-linked hydrophilic head groups so that no significant amount of active agent can leave the micelle by diffusion. Completely entrapped smaller guest molecules such as drugs and ligands are suitably "non-diffusable", by being entrapped wholly within the micelle. Completely entrapped larger agents such as proteins, polypeptides, DNA, RNA, and oligonucleotides are suitably non-diffusable by being entrapped wholly or partially so that the agent and micelle essentially cannot separate by diffusion. Completely entrapped agents cannot escape until the micelle itself has been degraded or the covalent cross-link bonds are cleaved under conditions of controlled release.

Cyclodextrin Micelle (CDM).

A cyclodextrin micelle (CDM) is a micelle that contains cyclodextrin derivatives including cyclodextrin dimers, trimers and polymers incorporated as amphiphilic molecules or where the cyclodextrin molecules are part of an amphiphilic polymer that forms the micelle aggregate.

Biocleavable Cyclodextrin Micelle.

A biocleavable cyclodextrin micelle (biocleavable CDM) is a new micelle composition provided by the instant invention. It is an embodiment of this invention comprising a CDM that further contains biocleavable or biodegradable linkages between the hydrophilic moieties that crosslink and stabilize the micelle. When loaded with active agent, the CDM is used as a micelle carrier for active agent. The crosslinks prevent any significant amount of active agent from dissociating from the micelle. As a carrier, the biocleavable CDM also provides the function or property of controlled release where the active agent is released upon lysis or cleavage of the biocleavable linkages. The most preferred carrier compositions are stable under physiological conditions such as in the bloodstream, but are biodegraded to release active agent when in contact with certain organs or tissues or when taken into certain cells or microorganisms.

Biocleavable Cyclodextrin Micelle Carrier.

A biocleavable cyclodextrin micelle carrier (CDM carrier) is a new micelle composition provided by the instant invention. It is defined herein as a CDM that has completely entrapped or incorporated a drug or other active agent. The active agent may be held as a "captured guest". The entrapment or "capture" of the active agent overcomes the problem in the prior art of the CD host and guest molecules separating by diffusion. Generally, the agent has also formed a noncovalent "inclusion complex", or "inclusion compound" with the cyclodextrins of the CDM.

In a preferred embodiment the capturing is accomplished through complete physical entrapment by the CDM carrier. In this embodiment, the active agent is "completely entrapped" as defined previously for biocleavable micelle carriers.

For the biocleavable CDM carriers of the instant invention, the guest molecules are completely entrapped during polymerization or during the final cross-linking step of making the carrier. Initially, guest molecules are mixed with the "open" components of the micelle, which may comprise amphiphilic cyclodextrin derivatives, amphiphilic cyclodextrin dimers, trimers or an open amphiphilic cyclodextrin polymer. An open cyclodextrin polymer means that the polymer is only partially cross-linked so that active agent can associate with the polymer and form complexes with member cyclodextrins. In the final synthesis step of the CDM carrier, the micelle is closed by additional covalent cross-linking which completely entraps the agent as defined previously.

Targeted Biocleavable Micelle or Biocleavable CDM Carriers.

A targeted biocleavable micelle carrier is an embodiment of this invention composed of a biocleavable micelle or a biocleavable CDM carrier that has a biorecognition molecule covalently coupled to its surface. However, the biorecognition molecule is not an inclusion complex within the micelle carrier. The carrier is thereby targeted through the specific binding properties of the biorecognition molecule coupled to the surface.

During the coupling, the functions of the biorecognition molecule and the targeted biocleavable micelle carrier are not irreversibly or adversely inhibited. Preferably, the biorecognition molecule maintains specific binding properties that are functionally identical or homologous to those it had before coupling. Preferably, the biorecognition molecule is coupled through a suitable spacer to avoid steric hindrance.

Targeted biocleavable micelle or biocleavable CDM carriers coupled to avidin and streptavidin are useful for subsequent noncovalent coupling to any suitable biotinylated substance. Similarly, biocleavable micelle or biocleavable CDM carriers coupled to antibody can be noncovalently coupled to another antibody, or to a nucleic acid or other suitable substance that has the appropriate biorecognition properties. Another useful cyclodextrin carrier comprises protein A, protein G, or any suitable lectin or polypeptide that has been covalently coupled to a biocleavable micelle or biocleavable CDM carrier.

Controlled Release.

For this invention, controlled release (or "active release") is defined as the release of an entrapped active agent from the biocleavable micelle carrier by cleavage of certain biocleavable covalent linkages that were used to entrap the active agent and/or synthesize the carrier. This definition specifically excludes any significant release by diffusion (i.e. passive), such as slow release, until said linkages are cleaved.

Biocleavable Cross-linking Agent.

A biocleavable cross-linking agent comprises a new invention for facilitating the synthesis of drug carriers with controlled release. In one embodiment it is comprised of a sequence of amino acids containing a biocleavable linkage, described previously, that has amino groups at each end for direct coupling to amino-reactive coupling agents. Using the convention of starting with the amino or "N" terminus on the left and the carboxyl or "C" terminus on the right, some examples are: Gly-Phe-Leu-Gly-Lys, or Lys-Gly-Phe-Leu-Gly-Lys. Another embodiment comprises a synthetic polypeptide with a biocleavable sequence as described, and also includes succinimide, N-succinimidyl, bromoacetyl, maleimide, N-maleimidyl, oxirane, p-nitrophenyl ester, or imidoester coupling groups on each end.

For acid-labile biocleavable cross-linking agents, one embodiment comprises a bifunctional coupling agent with a hydrazone linkage incorporated into it. For instance, it would comprise a hydrazone linkage between aliphatic (or aromatic) chains that have succinimide, N-succinimidyl, bromoacetyl, maleimide, N-maleimidyl, oxirane, or imidoester coupling groups on each end. Another embodiment comprises a bifunctional coupling agent with an ortho ester or poly(ortho ester) linkage incorporated into it with terminal coupling groups described previously.

One example for synthesizing an acid-labile biocleavable coupling agent is to first react an excess of hydrazinobenzoic acid with glutaraldehyde to couple one hydrazinobenzoic acid at each end of the dialdehyde. This produces hydrazone linkages with terminal carboxyl groups at each end. The terminal carboxyl groups are then converted to N-succinimidyl ester groups.

Coupling.

For the instant invention, two distinct types of coupling are defined. One type of coupling can be through noncovalent, "attractive" binding as with a guest molecule and cyclodextrin, antigen and antibody or biotin and avidin. Noncovalent coupling is binding between substances through ionic or hydrogen bonding or van der waals forces, and/or their hydrophobic or hydrophilic properties.

Unless stated otherwise, the preferred coupling used in the instant invention is through covalent, electron-pair bonds or linkages. Many methods and agents for covalently coupling (or crosslinking) amphiphilic molecules as well as cyclodextrins and cyclodextrin derivatives are known and, with appropriate modification, can be used to couple the desired substances through their "functional groups" for use in this invention. Where stability is desired, the preferred linkages are amide bonds, peptide bonds, ether bonds, and thio ether bonds, among others.

Functional Group.

A functional group is defined here as a potentially reactive site on a substance where one or more atoms are available for covalent coupling to some other substance. When needed, functional groups can be added to amphiphilic molecules and various substances through detivatization or substitution reactions.

Examples of functional groups are aldehydes, allyls, amines, amides, azides, carboxyls, carbonyls, epoxys (oxiranes), ethynyls, hydroxyls, ketones, certain metals, nitrenes, phosphates, propargyls, sulfhydryls, sulfonyls, phenolic hydroxyls, indoles, bromines, chlorines, iodines, and others. The prior art has shown that most, if not all of these functional groups can be incorporated into or added to amphiphilic molecules used to make micelles, and to cyclodextrins, biorecognition molecules, nucleic acids and support materials.

Cross-linking or Coupling Agent.

A coupling agent (or cross-linking agent), is defined as a chemical substance that produces and/or reacts with functional groups on a substance to produce covalent coupling, crosslinking, or conjugation with that substance. Because of the stability of covalent coupling, this is the preferred method. Depending on the chemical makeup or functional group on the amphiphilic molecule, cyclodextrin, nucleic acid, or biorecognition molecule, the appropriate coupling agent is used to provide the necessary active functional group or to react with the functional group. In certain preparations of the instant invention, coupling agents are needed that provide a "spacer" or "spacer arm" as described by O'Carra, P., et al, FEBS Lett. 43, 169(1974) between an amphiphilic molecule and a biorecognition molecule to overcome steric hindrance. Preferably, the spacer is a substance of 4 or more carbon atoms in length and can include aliphatic, aromatic and heterocyclic structures.

With appropriate modifications by one skilled in the art, the coupling methods referenced in U.S. Pat. No. 6,048,736 and PCT/US99/30820, including references contained therein, are applicable to the synthesis of the preparations and components of the instant invention and are hereby incorporated by reference.

Examples of energy activated coupling or cross-linking agents are ultraviolet (UV), visible and radioactive radiation that can promote coupling or crosslinking of suitably derivatized cyclodextrins. Examples are photochemical coupling agents disclosed in U.S. Pat. No. 4,737,454, among others. Also useful in synthesizing components of the instant invention are enzymes that produce covalent coupling such as nucleic acid polymerases and ligases, among others.

Amphiphilic molecules as well as amphiphilic cyclodextrin dimers, trimers and polymers are first prepared for use as the primary components to synthesize the biocleavable micelle or biocleavable CDM carriers. Examples are amphiphilic block polymers or amphiphilic CD-blocks. Useful derivatizing and/or coupling agents for preparing such block polymers are bifunctional, trifunctional or polyfunctional crosslinking agents that will covalendy couple to the hydroxyl groups of monomers as well as cyclodextrin. Some preferred examples are oxiranes such as epichlorohydrin, epoxides such as 1,4 butanediol diglycidyl ether (BDE), glycerol diglycidyl ether (GDE), trimethylolpropane triglycidyl ether (TMTE), glycerol propoxylated triglycidyl ether (GPTE), 1,3-butadiene diepoxide, triphenylolmethane triglycidyl ether, 4,4'-methylenebis (N,N-diglycidylaniline), tetraphenylolethane glycidyl ether, bisphenol A diglycidyl ether, bisphenol A propoxylate diglycidyl ether, bisphenol F diglycidyl ether, cyclohexanedimethanol diglycidyl ether, 2,2'-oxybis (6-oxabicyclo[3.1.0] hexane), polyoxyethylene bis(glycidyl ether), resorcinol diglycidyl ether, ethylene glycol diglycidyl ether (EGDE) and low molecular weight forms of poly(ethylene glycol) diglycidyl ethers or poly (propylene glycol) diglycidyl ethers, among others.

Other preferred derivatizing and/or coupling agents for hydroxyl groups are various disulfonyl compounds such as benzene-1,3-disulfonyl chloride and 4,4'-biphenyl disulfonyl chloride and also divinyl sulfone, among others.

Most preferred coupling agents are also chemical substances that can provide the biocompatible linkages for synthesizing the biocleavable micelle or biocleavable CDM carriers of the instant invention. Covalent coupling or conjugation can be done through functional groups using coupling agents such as glutaraldehyde, formaldehyde, cyanogen bromide, azides, p-benzoquinone, maleic or succinic anhydrides, carbodiimides, epichlorohydrin, ethyl chloroformate, dipyridyl disulfide and polyaldehydes.

Also most preferred are derivatizing and/or coupling agents that couple to thiol groups ("thiol-reactive") such as agents with any maleimide, vinylsulfonyl, bromoacetal or iodoacetal groups, including any bifunctional or polyfunctional forms. Examples are m-maleimido-benzoyl-N-hydroxysuccininide ester (MBS), succinimidyl 4-(N-maleimidomethyl) cyclohexane-1-carboxylate (SMCC), succinimidyl 4-(p-maleimidophenyl)butyrate (SMPB), dithiobis-N-ethylmaleinide (DTEM), 1,1'-(methylenedi-4,1-phenylene) bismaleimide (MPBM), o-phenylenebismaleimide, N-succinimidyl iodoacetate (SIA), N-succinimidyl-(4-vinylsulfonyl) benzoate (SVSB), and tris-(2-maleimidoethyl) amine (TMEA), among others.

Other coupling groups or agents useful in the instant invention are: p-nitrophenyl ester (ONp), bifunctional imidoesters such as dimethyl adipimidate (DMA), dimethyl pimelimidate (DMP), dimethyl suberimidate (DMS), methyl 4-mercaptobutytrimidate, dimethyl 3,3'-dithiobis-propionimidate (DTBP), and 2-iminothiolane (Traut's reagent);

bifunctional NHS esters such as disuccinimidyl suberate (DSS), bis[2-(succinimido-oxycarbonyloxy) ethyl] sulfone (BSOCOES), disuccinimidyl (N,N'-diacetylhomocystein) (DSAH), disuccinimidyl tartrate (DST), dithiobis(succinimidyl propionate) (DSP), and ethylene glycol bis(succinimidyl succinate) (EGS), including various derivatives such as their sulfo-forms;

heterobifunctional reagents such as N-5-azido-2-nitrobenzoyloxysuccinimide (ANB-NOS), p-azidophenacyl bromide, p-azidophenylglyoxal, 4-fluoro-3-nitrophenyl azide (FNPA), N-hydroxysuccinimidyl-4-azidobenzoate (HSAB), methyl-4-azidobenzoimidate (MABI), p-nitrophenyl 2-diazo-3,3,3-trifluoropropionate, N-succinimidyl-6 (4'-azido-2'-nitrophenylamino) hexanoate (Lomant's reagent II), N-succinimidyl (4-azidophenyldithio) propionate (SADP), N-succinimidyl-3-(2-pyridyldithio) propionate (SPDP), and N-(4-azidophenylthio) phthalimide (APTP), including various derivatives such as their sulfo-forms;

homobifunctional reagents such as 1,5-difluoro-2,4-dinitrobenzene, 4,4'-difluoro-3,3'-dinitrophenylsulfone, 4,4'-diisothiocyano-2,2'-disulfonic acid stilbene (DIDS), p-phenylene-diisothiocyanate (DITC), carbonylbis(L-methionine p-nitrophenyl ester), 4,4'-dithio-bisphenylazide and erythritolbiscarbonate, including various derivatives such as their sulfo-forms;

photoactive coupling agents such as N-5-azido-2-nitrobenzoylsuccinimide (ANB-NOS), p-azidophenacyl bromide (APB), p-azidophenyl glyoxal (APG), N-(4-azidophenylthio) phthalimide (APTP), 4,4'-dithio-bis-phenylazide (DTBPA), ethyl 4-azidophenyl-1,4-dithiobutyrimidate (EADB), 4-fluoro-3-nitrophenyl azide (FNPA), N-hydroxysuccinimidyl-4-azidobenzoate (HSAB), N-hydroxysuccinimidyl-4-azidosalicylic acid (NHS-ASA), methyl-4-azidobenzoimidate (MABI), p-nitrophenyl-2-diazo-3,3,3-trifluoropropionate (PNP-DTP), 2-diazo-3,3,3-trifluoropropionyl chloride, N-succinimidyl-6(4'-azido-2'-nitrophenylamino) hexanoate (SANPAH), N-succinimidyl(4-azidophenyl)1,
3'-dithiopropionate (SADP), sulfosuccinimidyl-2-(m-
azido-o-nitobenzamido)-ethyl-1,3'-dithiopropionate
(SAND), sulfosuccinimidyl(4-azidophenyldithio)
propionate (Sulfo-SADP), sulfosuccinimidyl-6-(4'-
azido2'-nitrophenylamino)hexanoate (Sulfo-
SANPAH), sulfosuccinimidyl-2-(p-azidosalicylamido)
ethyl-1,3'-dithiopropionate (SASD), and derivatives
and analogs of these reagents, among others. The
structures and references for use are given for many of
these reagents in, "Pierce Handbook and General
Catalog", Pierce Chemical Co., Rockford, Ill., 61105.

Amphiphilic Molecules For Micelle Preparation.

In the preferred aspects of this invention, amphiphilic molecules including amphiphilic block polymers or copolymers are first prepared for use as the primary components to synthesize the biocleavable micelle. Most preferred are amphiphilic diblock or triblock copolymers prepared from a variety of monomers to provide at least one hydrophilic and one hydrophobic moiety. For synthesis of biocleavable CDM carriers, amphiphilic cyclodextrin dimers, trimers and polymers as well as amphiphilic block copolymers that contain cyclodextrin dimers, trimers and polymers are used.

Such amphiphilic molecules and block polymers can function as an intermediate substance or "intermediate". The intermediate can function as a polymer "backbone" to which many cyclodextrin dimers, trimers or polymers are covalendy coupled to form a larger polymer. The intermediate can be included with cyclodextrin derivatives as another monomer to be copolymerized with the cyclodextrin derivatives (i.e. heteropolymer).

By definition, amphiphilic molecules and intermediate substances are bio-compatible in being suitably nonimmunogenic and nonallergenic. They can also provide improved structural properties, increase solubility or lower toxicity.

Amphiphilic molecules and copolymers can also introduce certain other desirable properties, such as a positive or negative net charge, or more efficient light energy transfer for photodynamic therapy. The desired biorecognition molecule or other substance can be coupled to available sites on the hydrophilic moieties of the amphiphilic molecule. Then, when the amphiphilic molecule is incorporated into a micelle, the biorecognition molecule is thereby coupled to the biocleavable micelle or biocleavable CDM carrier of the instant invention.

Examples of suitable substances for use in amphiphilic molecules are certain proteins, polypeptides, polyamino acids, glycoproteins, lipoproteins (i.e. low density lipoprotein), nucleic acid polymers, DNA, RNA, amino sugars, glucosamines, polysaccharides, lipopolysaccharides, amino polysaccharides, polyglutamic acids, poly lactic acids (PLA), polylysines, polyethylenimines, polyacrylamides, nylons, poly(allylamines), lipids, glycolipids and suitable synthetic polymers, especially biopolymers, resins and surfactants, as well as suitable derivatives of these substances. Also included as suitable substances are the polymers disclosed in U.S. Pat. No. 4,645,646. Also preferred for use in amphiphilic molecules are N-(2-hydroxypropyl) methacrylamide (HPMA), HPMA derivatives, poly cyanoacrylates such as poly(butyl cyanoacrylate), poly (isobutyl or isohexyl cyanoacrylate), polyethylene glycol (PEG), any micelle-forming PEG derivatives, poly (D,L-lactic-coglycolic acid) (PLGA), PLGA derivatives and poly (D,L-lactide)-block-methoxypolyethylene glycol (diblock).

Also included are any micelle-forming copolymers that contain poly(ethylene oxide) (PEO) such as PEO-block-poly(L lysine), PEO-block-poly(aspartate), PEO-block-poly (beta-benzyl aspartate), PEO-block-poly(L-lactic acid), PEO-block-poly(L-lactic-coglycolic acid), PEO-blockpoly (propylene oxide) (PPO) and any derivatives. Also preferred are any micelle-forming triblock copolymers (Pluronics) that contain PEO and polypropylene oxide) (PPO), such as PEO-block-PPO-block-PEO in various ratios. Specific examples are the F, L or P series of Pluronics including F-68, F-108, F-127, L-61, L-121, P-85, and any derivatives.

The micelles of this invention require the capacity for crosslinking hydrophilic moieties in the micelle. Through suitable derivatization and/or protection schemes, the desired biocleavable linkages or coupling groups can be incorporated into certain hydrophilic monomers for use in synthesizing diblock and triblock copolymers. Then, with suitable modification of the synthesis methods referenced by G. S. Kwon, IN: Critical Reviews in Therapeutic drug Carrier Systems, 15(5):481-512 (1998), suitable amphiphilic molecules can be synthesized for preparing the micelles of this invention. Diblock and triblock copolymer synthesis methods include ring-opening polymerization such as with PEO and various N carboxyanhydride (NCA) monomers; polymerizations using triphosgenes and organo-metal (i.e. nickel) initiators (i.e. stannous octoate). Also useful are anionic, zwitterionic and free radical polymerizations and transesterifications, among others.

Various materials may be incorporated into the components of the instant invention to produce new inventions with unexpected properties for use in certain applications. For instance, the addition of ferrous or magnetic particles may be used to give biocleavable micelle or biocleavable CDM carriers and other types of polymers (i.e. HPMA, PEG), magnetic properties (Ithakissios, D. S., Clin. Chim. Acta 84(1-2), 69-84, 1978). This would be useful for various in vivo manipulations such as using magnetic fields to localize or concentrate a magnetic micelle drug carrier in a specific part of the body. Also, the magnetic particle micelles may be used in diagnostic imaging or to trigger the desired effect (i.e. cytotoxic on cancer cells) such as by vibrating or rotating or lysing the micelles to release active agent or prodrug using alternating magnetic fields.

EXAMPLES OF THE BEST MODES FOR CARRYING OUT THE INVENTION

In the examples to follow, percentages are by weight unless indicated otherwise. During the synthesis of the compositions of the instant invention, it will be understood by those skilled in the art of organic synthesis, that there are certain limitations and conditions as to what compositions will comprise a suitable micelle carrier and may therefore be prepared mutatis mutandis. It will also be understood in the art of cyclodextrins that there are limitations as to which drugs and other agents can be used to form inclusion complexes with certain cyclodextrins.

Specifically, it is known that smaller, alpha cyclodextrins are preferably used to complex with the smaller drugs or active agents. Whereas larger cyclodextrins are less limited, except that a "close fit" is generally preferred for stronger complexing affinity.

The terms "suitable" and "appropriate" refer to synthesis methods known to those skilled in the art that are needed to perform the described reaction or procedure. In the references to follow, the methods are hereby incorporated herein by reference. For example, organic synthesis reactions, including cited references therein, that can be useful in the instant invention are described in "The Merck Index", 9, pages ONR-1 to ONR-98, Merck & Co., Rahway, N.J. (1976), and suitable protective methods are described by T.

W. Greene, "Protective Groups in Organic Synthesis", Wiley-Interscience, NY (1981), among others. For synthesis of nucleic acid probes, sequencing and hybridization methods, see "Molecular Cloning", 2nd edition, T. Maniatis, et al, Eds., Cold Spring Harbor Lab., Cold Spring Harbor, N.Y. (1989).

All reagents and substances listed, unless noted otherwise, are commercially available from Aldrich Chemical Co., Wis. 53233; Sigma Chemical Co., Mo. 63178; Pierce Chemical Co., Ill. 61105; Eastman Kodak Co., Rochester, N.Y.; Pharmatec Inc., Alachua Fla. 32615; and Research Organics, Cleveland, Ohio. Or, the substances are available or can be synthesized through referenced methods, including "The Merck Index", 9, Merck & Co., Rahway, N.J. (1976). Additional references cited in U.S. Pat. No. 6,048,736 and PCT/US99/30820, are hereby incorporated herein by reference.

Biocleavable Micelle and Biocleavable CDM Carriers

The purpose is to provide a biocleavable micelle or biocleavable CDM carrier that has an active agent completely entrapped within. For synthesis, the general approach is; (1) to produce or modify or protect, as needed, one or more functional or coupling groups on the hydrophilic moiety of micelle-forming amphiphilic molecules or copolymers or amphiphilic cyclodextrin components, consisting of cyclodextrins, or open CD dimets, trimers or polymers; (2) combine under appropriate conditions, the micelle-forming amphiphilic molecules or copolymers with a drug or active agent to produce a micelle that has entrapped the active agent within the micelle and (3) using various coupling methods cross-link the hydrophilic moieties of the micelle to produce a biocleavable micelle carrier that completely entraps the drug within the biocleavable micelle or biocleavable CDM.

Also, as described below, the biocleavable micelle or biocleavable CDM carrier may be suitably derivatized to include other useful substances and/or chemical groups (e.g. biorecognition molecules, antenna, and catalytic substances), to perform a particular function. Depending on the requirements for chemical synthesis, the derivatization can be done before entrapment or afterward, using suitable protection and deprotection methods as needed.

Since cyclodextrins are composed of carbohydrates, they can be suitably derivatized and coupled through well-known procedures used for other carbohydrates, especially through available hydroxyl groups. For instance, vicinal hydroxyl groups on the cyclodextrin can be appropriately oxidized to produce aldehydes.

In addition, any functional group can be suitably added through well-known methods while preserving the cyclodextrin structure and complexing properties. Examples are: amidation, esterification, acylation, N-alkylation, allylation, ethynylation, oxidation, halogenation, hydrolysis, reactions with anhydrides, or hydrazines and other amines, including the formation of acetals, aldehydes, amides, imides, carbonyls, esters, isopropylidenes, nitrenes, osazones, oximes, propargyls, sulfonates, sulfonyls, sulfonamides, nitrates, carbonates, metal salts, hydrazones, glycosones, mercaptals, and suitable combinations of these. The functional groups are then available for the cross-linking of one or more cyclodextrin molecules using a bifunctional reagent.

Additional examples of cyclodextrins, inclusion compounds and catalytic groups including chemical methods for modifying and/or derivatizing cyclodextrins that are useful in the instant invention are described and referenced in U.S. Pat. No. 6,048,736 and PCT/US99/30820, which are incorporated herein by reference.

Suitable coupling or cross-linking agents for preparing the micelle carriers of the instant invention can be a variety of reagents previously described, including well known crosslinkers used to polymerize cyclodextrins. Other suitable crosslinkers or derivatizers are various epoxy compounds including propylene oxide, 1,2-diethoxyethane, 1,2, 7,8-diepoxyoctane, 2,3-epoxy-1-propanol (glycidol), glycerol propoxylate triglycidylether and 1,4-butanediol diglycidyl ether. Also useful are methods employing acrylic esters such as m-nitrophenyl acrylates, and hexamethylenediamine and p-xylylenediamine complexes, and aldehydes, ketones, alkyl halides, acyl halides, silicon halides, isothiocyanates, and epoxides.

Methods for Derivatizing Cyclodextrins

For synthesizing the biocleavable CDM carriers of this invention, individual cyclodextrin derivatives (i.e. monomer) as well as dimers, trimers and polymers are the primary components or units used. Although native cyclodextrins are useful for synthesizing the carriers, many other useful properties can be incorporated into the carriers by first derivatizing the cyclodextrin components before making the polymers. Derivatizing is defined as the chemical modification of a CD through addition of any functional or coupling group and/or other substance. Generally, derivatized cyclodextrins can be used to facilitate cross-linking reactions and introduce functional groups for use during or after the carrier is prepared. Frequently, an integral part of using derivatized cyclodextrins involves protecting certain functional groups during certain cross-linking steps and then deprotecting those groups for use in subsequent steps.

A. Protected Hydroxyl Groups.

Primary and/or secondary hydroxyl groups on the cyclodextrin (or derivatives), can be selectively protected and deprotected using known methods during derivatizing and/or capping procedures, to provide selective coupling at the primary or secondary end of the CD molecule, as desired. For instance, formation of protective esters (e.g. benzoates using benzoyl chloride), and selective cleavage (deprotection), of primary esters using anhydrous alcoholysis provides mostly primary hydroxyls for derivatization. After derivatization and/or coupling the primary hydroxyls, the secondary hydroxyls can be deprotected for additional detivatization, coupling and/or capping.

Preferred hydroxyl protection schemes include various methods for silylation of the primary hydroxyls using tert-butyldimethylsilyl chloride (TBDMS), (K. Takeo, et al., Carbohydrate Res. 187, 203 (1989)) for detivatization of the secondary hydroxyls. Or, the use of sodium hydride with TBDMS (S. Tian, et al., Tetrahedron Lett. 35, 9339(1994)) to protect secondary hydroxyls during derivatization of the primary hydroxyls. The silyl groups are then removed by treatment with tert-butylammonium fluoride.

B. Preparation of Sulfonylated Cyclodextrin.

A variety of suitable methods are available for sulfonylation of CD or CD polymer before or after protection of specific hydroxyl groups and/or capping of the CD. Suitably, CD polymer (10 gm), is combined with a suitable sulfonylating reagent (20 gm), such as p-toluenesulfonyl (tosyl) chloride, mesitylenesulfonyl chloride or naphthalenesulfonyl chloride, among others, in anhydrous pyridine, for 3-5 Hrs at room temperature (RT).

C. Preparation of Dialdehyde Cyclodextrin (Dial-CD).

A dialdehyde CD derivative (dial-CD) and dialdehyde cyclodextrin polymer (dial-CD polymer) is prepared by oxidation using known methods with sodium metaperiodate in water or suitable buffer solution (e.g. 0.2 M phosphate saline, pH 5–7). For use in preparing biocleavable CDM carriers, dial-CD can also include oxidized forms of HPCD, DHPCD and SBE-CD.

D. Amino-Cyclodextrin (Amino-CD) Derivatives.

Amino groups can be introduced into CD polymer by reaction of a sulfonylated CD polymer with azide compounds including hydrazine, and 2,6-bis(4-azidobenzylidene)-4methylcyclohexanone, or coupling to diamines. Also, when desired, a "monoamino" CD, wherein one amino group has been coupled, can be prepared through known methods, including limited or sterically determined monosulfonylation, and/or by specific protection and deprotection schemes. An amino-CD or amino-CD polymer, is suitably protected and/or deprotected as needed.

E. Diamino Derivatives.

A previously sulfonylated CD or CD polymer is suitably iodinated so that it will couple to primary amino groups, using known methods. Suitably, 10 gm of sulfonylated CD or CD polymer is combined with 12 gm of NaI on 200 ml of methanol, and mix at 70° C. for 48–60 Hrs. The iodinated CD product is collected by precipitation with acetone and purified by column chromatography.

The iodinated CD or CD polymer is coupled through an amino group to a suitable diamino substance. Suitable diamino substances are; 1,4-diaminobutane, 1,6-diaminohexane, 1,7-diaminoheptane, 1,8-diaminooctane, 1,10-diaminodecane, 1,12-diaminododecane, and other aliphatic, or aromatic, or heterocyclic carboxylic acids with two available amino groups for coupling. Coupling is done in a suitable solvent such as dimethylformamide (DMF), mixing 10 gm of iodinated CD polymer with a molar excess of the diamino substance (e.g. 10–20 gm of 1,6-diaminohexane), at 100° C. for 24 Hrs. The product, amino-CD (or amino-CD polymer), is concentrated and purified by column chromatography.

F. Protected Amino Groups.

The amino groups introduced by various methods can be suitably protected by reaction with a halogenated alkylphthalimide such as N-(4-bromobutyl)phthalimide. After other suitable detivatizing, coupling and/or capping has been done, an amino group is deprotected by reaction with hydrazine in suitable solvent.

Also, the diamino substances of various chain lengths can be suitably derivatized before coupling. For instance, they can be "half protected" as trifluoroacetamidoalkanes at one of the amino ends, as described by Guilford, H., et al, Biochem. Soc. Trans. 3, 438 (1975), before coupling, and then suitably deprotected such as by hydrolysis or alcoholysis. Yet another suitable method involves the coupling of THP-protected amino-alkynes, previously described, to the iodinated CD or CD polymer and subsequent deprotection as needed.

G. Sulfhydryl-Cyclodextrin (SH-CD) Derivatives.

A sulfhydryl group can be added to an amino-CD, suitably prepared as described previously, by coupling the appropriate thiolating agent to the available amino group. For instance, thiolation of amino groups on amino-CD can be done by known methods using S-acetylmercaptosuccinic anhydride (SAMSA), SIAB, or 2-iminothiolane. The sulfhydryl is protected as a disulfide during subsequent coupling reactions until it is exposed through disulfide cleavage.

Sulfhydryls can also be introduced through reaction of available hydroxyls with a suitable epoxy compound. For instance, epichlorohydrin or a suitable diepoxy crosslinker previously described, is coupled to a CD or CD polymer wherein free epoxy groups are produced. Free epoxy groups are then reacted with sodium thiosulfate to give thiosulfate esters. The thiosulfate esters are subsequently reduced to sulfhydryls with dithiothreitol.

Thiosulfate groups can also be introduced by coupling 1,3-propane sultone or 1,4-butane sultone directly to the hydroxyl groups on the cyclodextrin or CD dimer, trimer or polymer. The thiosulfate esters are subsequently reduced to sulfhydryls with dithiothreitol.

H. Thiosulfate-Cyclodextrin (TS-CD) Derivatives.

Thiosulfate groups can also be introduced by reacting primary or secondary hydroxyl groups with various cyclic sultone compounds to produce sulfoalkyl ether derivatives. For instance, 1,4-butane sultone reacts with the hydroxyl groups to produce a sulfobutyl ether derivative (Stella, et al. U.S. Pat. No. 5,134,127), or 1,3-propane sultone reacts with the hydroxyl groups to produce a sulfopropyl ether derivative.

New, more useful materials with higher binding affinities than derivatives of single CD molecules can be synthesized by first preparing CD dimers, trimers or polymers of cyclodextrin by crosslinking the cyclodextrins by various means. For instance crosslinking is done using bifunctional or multifunctional epoxy crosslinkers such as epichlorohydrin, 2,3 epoxy-1,4butanedione, glycerol diglycidyl ether, or glycerol propoxylate triglycidyl ether, among others. Then the crosslinked products are reacted with a cyclic sultone such as 1,4-butane or 1,3propane sultone in basic conditions such as 1-50% NaOH in water. The resulting derivative is generally more soluble that the initial crosslinked cyclodextrin and is cationic to allow migration in an electric field.

I. Preparation of Carboxylic Acid CD Derivatives.

A preferred method for adding carboxylate groups is to couple glutaric or succinic anhydride to a hydroxyl group on the CD, or CD dimer, trimer or polymer. This produces a terminal carboxylate, which can then be protected by esterification as needed. Also, carboxylates can be derivatized to an NHS ester using N-hydroxysuccinimide and carbodiimide such as dicyclohexyl carbodiimide.

Alternatively, a previously sulfonylated CD or CD polymer can be suitably iodinated as previously described for diamino groups. An iodinated CD polymer or a dial-CD polymer is coupled through the amino group to a suitable amino-carboxylic acid to provide the desired length of spacer. Suitable amino-carboxylic acids are; 4-aminobutyric acid, 6-aminohexanoic acid, 7-aminoheptanoic acid, 8-aminocaprylic acid, 12-aminododecanoic acid, and other aliphatic, or aromatic, or heterocyclic carboxylic acids with an available amino group for coupling.

Coupling of amino-carboxylic acid to iodinated CD or CD polymer is done in a suitable solvent such as dimethylformamide (DMF), mixing 10 gm of iodinated CD polymer with a molar excess of amino-carboxylic acid (e.g. 10 gm of 6-aminohexanoic acid), at 100° C. for 24 Hrs. The product, CD-carboxylic acid, is concentrated and purified by column chromatography.

Coupling of amino-carboxylic acid to dial-CD or dial-CD polymer is done by reductive alkylation. In a suitable buffer (e.g. 0.1 M borate, pH 7.5–8.5), 0.1–0.5 M triethanolamine), 10 gm of dial CD polymer is mixed with a molar excess of amino-carboxylic acid (e.g. 10 gm of 12-aminodecanoic acid), at RT for 1–2 Hrs. The Schiffs base coupling is stabilized by suitable reduction with $NaBH_4$ (e.g. 0.1–1 mg/ml), for 1–12 Hrs. The product, CD-carboxylic acid, is concentrated and purified by column chromatography and dried for subsequent reactions as needed.

J. Capping Cyclodextrins.

Capping is a type of derivatizing defined herein as coupling any suitable chemical "capping substance" to two or more sites on the CD molecule so that the substance spans the area between the coupled sites. Preferably, the capping substance spans across one of the end openings of the CD molecule and thereby stops the passage of a guest molecule through the capped CD molecule.

It is well known that capping with disulfonyl chloride compounds is also useful for synthesizing bifunctional derivatives of cyclodextrins. For instance, when the CD has been capped with a suitable disulfonyl compound, it is coupled at two of the available hydroxyl groups. These two coupled sites can then be disubstituted to introduce various thiol or amino groups through nucleophilic displacement. For instance, displacement with ammonia gives amino groups, displacement with hydrogen sulfide gives thiol groups.

The CD's used herein can be suitably complexed with one or more guest molecules and/or derivatized and/or capped before, during or after their incorporation into the water-soluble CD polymer carrier of the instant invention. In addition, the derivatizing and/or capping can be a done to produce CD's with the desired substances coupled to specific locations on the CD molecule. In the preparation of CD derivatives for use as hosts for drugs or other agents, modifications that increase affinity between the host CD and guest(s) are preferred. For instance, the host CD's of this invention are preferably derivatized (e.g. methylated or benzylated), and/or capped by various means to increase host-guest affinity.

K. Derivatizing and Capping Substances.

Preferably, the capping substance is coupled at the primary or secondary "end" of the CD molecule, forming a bridge across either (or both) opening(s) that includes suitable hydrophobic groups in the capping substance. The capping substances can be coupled directly to available hydroxyls on the CD, or they can be coupled to suitable functional groups such as; diamino (or triamino), compounds to iodinated CD, or azido compounds to sulfonylated hydroxyls, and/or through "spacers" added to the CD.

Suitable disulfonyl capping substances are biphenyl-4,4'-disulfonyl chloride, 1,3-benzene disulfonyl chloride, 2,4-mesitylene disulfonyl chloride, 2,6-naphthalene disulfonyl chloride, 4,4'-oxybis(benzene sulfonyl chloride), 4,4'-methylene bis(benzene sulfonyl chloride), m,m'-benzophenone-disulfonyl chloride, p,p'-stilbene-disulfonyl chloride, and diphenylnethane-p,p'-disulfonyl chloride, among others. Other suitable capping substances are imidazoles, 6-methylamino-deoxy and 6-methylamino-6-deoxy derivatives transformed to the corresponding N-formyl compounds, terephthaloyl chloride, dianhydrides such as 3,3',4,4'-benzophenonetetracarboxylic dianhydride and 3,4,9,10-perylenetetracarboxylic anhydride, azido compounds such as 2,6-bis(4-azidobenzylidene)-4-methylcyclohexanone, and derivatives of aurintricarboxylic acid (e.g. thionyl chloride derivatives, triammonium salts "aluminons"), among others.

L. Cyclodextrin Blocks.

Cyclodextrin blocks (CD block) are compositions that provide for the incorporation of cyclodextrin derivatives into micelle-forming amphiphilic molecules through copolymerization with other polymer blocks. The CD blocks can include CD dimers, CD trimers or CD polymers. The CD blocks can be primarily hydrophilic to produce micelles with the CD moieties in the hydrophilic shell. Or, the CD blocks can be primarily hydrophobic to produce micelles with the CD moieties in the hydrophobic core.

To produce micelle-forming diblock or triblock amphiphilic molecules using CD blocks, the cyclodextrins can be suitably derivatized and/or protected as previously described or referenced. The CD blocks also have available suitable reactive groups that can copolymenze with other block polymers, using suitably modified methods described and referenced by G. S. Kwon, IN: Critical Reviews in Therapeutic drug Carrier Systems, 15(5):481-512 (1998).

For example, a CD derivative (i.e. CD dimer) is prepared and made hydrophobic by adding alkyl or aromatic groups (i.e. methylation, ethylation, or benzylation), and also has available an N carboxyanhydride (NCA) group coupled through a suitable spacer.

One form of CD block would be: Methylated-CD-CD-poly(aspartate)$_N$-NCA

This CD block (where N=1–10) can then be copolymerized with suitable blocks of alphaMethyl-omega-Amino-Poly(ethylene oxide) (PEO) in suitable solvent ($CHCl_3$:DMF) to produce a micelle-forming diblock amphiphilic molecule. The resulting diblock is: CD-block-PEO. With suitable modifications PEG can be used in place of PEO. Also, triblocks such as PEO-block-CD-block-PEO can be prepared.

Other combinations for the CD-blocks of this invention can include the covalent coupling of an alpha CD with a beta CD, an alpha CD with a gamma CD, a beta CD with a gamma CD and polymers with various ratios of alpha, beta and gamma cyclodextrins.

Preparation I

Surfactant with Biocleavable Linkages

The purpose is to prepare a surfactant that is amphiphilic and contains a biocleavable moiety on the hydrophilic head group that can be crosslinked with similar surfactants when incorporated into a micelle (CD24).

In this example, polyoxyethylene sorbitan monolaurate (Tween 20) is coupled to glycidol through available hydroxyl groups on the hydrophilic head (polyoxyethylene sorbitan), to provide dihydroxypropyl moieties with terminal diol groups. The diol groups are then oxidized to produce terminal aldehyde groups, are then coupled to hydrazine to provide acid-labile hydrazone linkages.

In about 50 ml of water, 5 gm of Tween 20 was dissolved and neutralized to pH 7 with NaOH and 3 ml of glycidol was added, mixed and allowed to react overnight at rt. To this solution, a total of 4 gm of $NaIO_4$ was added, dissolved and allowed to oxidize several days at rt. The product is preferably isolated after dialysis against water. The product was concentrated by evaporation and precipitated in approximately 90% isopropanol at 0° C., and dried. The oxidized product is dissolved in water, then reacted with an excess of hydrazine (3 ml of 64% hydrazine hydrate) and purified to produce hydrazine-linked Tween 20 (Hz-Tw). The resulting surfactant contains acid-labile hydrazone linkages coupled to the hydrophilic head with terminal amino groups. The surfactant can now be used to prepare micelles containing an active agent and the amino groups can then be suitably crosslinked. Also, the amino groups can be thiolated using 2-iminothiolane to provide thiols for crosslinking.

Alternatively, the hydrophilic head group can be suitably derivatized with other coupling groups such as succinimide, N-succinimidyl, bromoacetyl, maleimide, N-maleimidyl, oxirane, pnitrophenyl ester, or imidoester.

Alternatively, any suitable diamino compound can be used in place of hydrazine, then $NaBH_4$ reduced to stabilize. Also, the terminal aldehyde groups can be coupled to a diamino, Fmoc half-protected polypeptide containing any suitable biocleavable sequence such as Phe-Leu, Leu-Phe or Phe-Phe, among others. The Fmoc groups are then removed to provide unprotected amino groups for subsequent crosslinking with or without suitable thiolation.

Also, other surfactants with hydroxyl groups can be suitably substituted for the Tween 20 such as Tween 40, 60 or 80, or sorbitan monolaurate, sorbitan monooleate, sorbitan monopalmitate (Span 20, 40, and 80), among others. The vicinal hydroxyls in Span 20, 40, and 80 can be suitably oxidized directly to produce dialdehydes that are coupled to hydrazine or other amines as described.

Preparation II

A Biocleavable Surfactant Crosslinked to Entrap Amphotericin

In this example hydrazine-linked Tween 20 is thiolated and used to entrap amphotericin B in micelles. The micelles are then crosslinked through the thiol groups to form a polymer.

Thiolated surfactant was prepared from about 2.3 gm of hydrazine-linked Tween 20 in 5 ml of water containing 0.2 M potassium phosphate buffer adjusted to pH 10 with NaOH. To this was added about 0.2 gm of 2-iminothiolane (Sigtna), mixed to dissolve and left to react overnight. The isolated surfactant product contains acid-labile hydrazone linkages coupled to the hydrophilic head with terminal thiol groups.

For preparation of amphotericin-loaded micelles, about 45 mg of thiolated surfactant was dissolved in about 0.3 ml of 50% dimethylformamide (DMF) in 0.0125 M potassium phosphate buffered water, pH 6.5. Then about 0.76 mg of citraconic anhydride-treated amphotericin B in 0.05 ml of DMF was added and mixed, resulting in a yellow suspension. The final volume was adjusted to 0.5 ml with 50% DMF.

For crosslinking, about 1.8 mg of 1,1'(methylenedi-4,1-phenylene) bismaleimide IPBM) dissolved in 0.025 ml DMF was added, mixed and left overnight. A yellow, polymerized precipitate was separated by centrifugation and the supernatant removed. The precipitate was further crosslinked with 1.4 mg of MPBM in 0.020 ml DMF for 2 hours. The precipitate was then washed 3 times by mixing and soaking it in 1 ml of 50% DMF, centrifuging and removing the supernatant. After the third wash, the precipitate was still very yellow due to amphotericin while the supernatant was only slightly yellow and clear. This showed that the crosslinked surfactant had entrapped a significant amount of amphotericin that was not readily extracted.

Preparation III

Amphiphilic Cyclodextrin Polymer

The purpose is to prepare a mixture of micelle-forming, amphiphilic cyclodextrin dimers, trimers and polymers with alkyl carbon chains attached. The cyclodextrins are cross-linked through hydroxyl groups using 1,4 butanediol diglycidyl ether (BDE) at low pH to favor reaction at the primary hydroxyl groups. Excess BDE molecules coupled at one end to the CD provide terminal oxirane groups that are subsequently thiolated by reaction with thiosulfate and reduction. Alkyl carbon chains are coupled to the CD derivatives using a "long chain epoxy" that couples to other available hydroxyl groups (CD88).

A. Cross-linking with BDE.

Into 125 ml of hot water (70–80° C.) adjusted to pH 4.5–5 with 0.05 ml 6 N HCl, was dissolved 2.84 gm of beta cyclodextrin (0.0025 moles). To this solution 4.1 ml of BDE (about 0.0125 moles) was added with mixing and continued heating for about 2 hours.

B. Coupling with a Long Chain Epoxy.

The mixture was adjusted to pH >10 with KOH and 1.28 gm (about 0.005 moles) of dodecyl/tetradecyl glycidyl ether (DTGE) was added and mixed vigorously. The solution was periodically mixed for about 1.5 hours, heated for about 3 hours and then left at room temperature (rt) overnight. The resulting solution was light yellow and turbid.

C. Coupling with Na Thiosulfate.

To the reheated mixture, 6 gm (about 0.025 moles) of sodium thiosulfate was added and mixed. After about 1 hour, the pH was adjusted to 7 with KOH and the solution was heated for about 3.5 hours more. Excess DTGE was removed by chilling to solidify the DTGE and the solution was decanted.

D. Dialysis.

The mixture was dialyzed against a continuous flow of distilled water in 500 mwco tubing (Spectra/Por CE) for about 40 hours. The solution was concentrated by evaporation to 8 ml to give a clear, light yellow solution.

E. Reduction with Dithiothreitol.

To the mixture, 8 ml of water and 0.96 gm (about 0.0062 moles) of dithiothreitol (DTT) was added, mixed and left overnight. The turbid solution was then dialyzed against a continuous flow of distilled water in 500 mwco tubing (Spectra/Pot CE) for about 40 hours. The solution was concentrated by evaporation to 3.7 ml to give a clear, yellow solution. Total yield based on dry weight was 2.276 gm.

F. Column Chromatography and Testing.

The mixture was fractionated on a Sephadex™ G15 column (2.5×47 cm) in water. The fractions were tested for relative carbohydrate and thiol concentration.

Carbohydrate was tested for by combining: 0.012 ml of sample, 0.01 ml of 1.5% 1-naphthol in methanol and finally 0.1 ml of 36N $H_2SO_4$ to produce a color reaction. The absorbance was read at 620 nm and sample carbohydrate concentration was calculated by linear regression using values from a cyclodextrin standard curve.

Thiol groups were tested for by combining: 0.008 ml of sample and 0.1 ml of 0.0125% 2,2'-dithio-bis(5-nitropyridine) (DTNP) in 62.5% isopropanol, pH 6 to produce a color reaction. The absorbance was read at 405 nm and sample thiol concentration was calculated by linear regression using values from a cysteine standard curve.

Fractions with corresponding peak concentrations of carbohydrate and thiol were pooled and concentrated by evaporation. The final volume was 2.2 ml and the total yield based on dry weight was 1.144 gm. The resulting amphiphilic CD polymer was highly water soluble and amorphous (glassy) when dried.

Alternatively, to produce other suitable hydrophobic cyclodextrin derivatives, other alkyl chains can be introduced by substituting suitable alkyl epoxy compounds for the one used in this example. For instance 1,2-epoxy derivatives of any suitable alkane such as propane, butane, pentane, hexane, octane, decane and dodecane can be substituted. Other useful epoxies such as glycidyl isopropyl ether, glycidyl methacrylate and glycidyl tosylate can be substituted. Also certain aromatic epoxies or heterocyclic epoxies can be substituted such as benzyl glycidyl ether, (2,3-epoxypropyl) benzene, 1,2-epoxy-3-phenoxypropane, exo-2,3-epoxynorborane, among others.

Alternatively, the CD polymer can be suitably derivatized with other coupling groups such as succinimide, N-succinimidyl, bromoacetyl, maleimide, N-maleiniidyl, oxirane, p-nitrophenyl ester, or imidoester. Also, the CD polymer can be coupled to a polypeptide containing any suitable biocleavable sequence such as Phe-Leu, Leu-Phe or Phe-Phe, among others. Also, the CD polymer can be suitably derivatized to provide a CD-block with an N carboxyanhydride for subsequent copolymerization into PEO-block copolymers.

Combinations for this invention can include the covalent coupling of an alpha CD with a beta CD, an alpha CD with a gamma CD, a beta CD with a gamma CD and polymers with various ratios of alpha, beta and gamma cyclodextrins.

PREPARATION IV

Amphiphilic Cyclodextrin Polymer Used to Entrap Camptothecin

The purpose is to prepare a biocleavable CDM carrier with completely entrapped camptothecin using a thiolated amphiphilic cyclodextrin monomer crosslinked with 1,1'-(methylenedi-4,1-phenylene) bismaleimide (MPBM) (CD90).

In about 0.3 ml of water, 0.05 gm of thiolated cyclodextrin monomer was combined with a total of about 3 micrograms of camptothecin and the solution was mixed to solubilize the drug. This mixture was then crosslinked by adding about 150 micrograms of MPBM, mixed and left overnight. The slightly turbid solution was exhaustively dialyzed in 2,000 molecule weight cutoff tubing, first against 50% and then 45% isopropanol in water, overnight. The resulting solution had a strong blue fluorescence over UV light, showing that camptothecin was entrapped in the crosslinked polymer in the dialysate. Dialysis was continued in 22% isopropanol for 3 hours, then in water for 2 more hours.

The dialysate was then assayed for drug using a fluorescent assay vs. a camptothecin standard curve. The measured concentration of entrapped camptothecin in the drug-loaded carrier was 4.5 weight percent.

PREPARATION V

Coupling Methods for Targeting Biocleavable Micelle or Biocleavable CDM Carriers These are methods for synthesizing biocleavable micelle or biocleavable CDM carriers wherein a coupling group is included in the hydrophilic moiety of the composition to provide for coupling to any suitable biorecognition molecule with a suitable functional group. The biorecognition molecule can be a suitable protein, including antibodies, lectins, avidins and streptavidin, or ligands, or nucleic acids.

A. Preparation of NHS-Micelle Carriers.

An amphiphilic molecule (i.e. amphiphilic CD) with available carboxylate groups on the hydrophilic head is derivatized to provide an NHS ester. In a suitable anhydrous solvent such as DMF, the amphiphilic CD-carboxylic acid polymer is combined with N-hydroxysuccinimide and an aromatic carbodiimide such as N,N-dicyclohexylcarbodiimide, at approximately equimolar ratios and reacted at RT for 1–3 Hrs. The product, N-hydroxysuccinimide polycyclodextrin (NHS-polyCD), is separated in the filtrate from precipitated dicyclohexylurea, collected by evaporation and purified by chromatography.

Under appropriate conditions, NHS-polyCD derivatives can be prepared by coupling NHS esters directly to amphiphillic amino-CD polymer. Preferably, the NHS ester is a bifunctional NHS coupling agent with a suitable spacer. Suitable NHS coupling agents for use in this invention have been previously described, including DSS, bis (sulfosuccinimidyl)suberate ($BS^3$), DSP, DTSSP, SPDP, BSOCOES, DSAH, DST, and EGS, among others.

B. Preparation of Sulfhydryl-CD Polymer Carriers.

Sulfhydryls on polymer carriers can be used for disulfide coupling to other available sulfhydryls on the desired biorecognition molecule such as antibodies, or avidins, or streptavidin, or ligands, or nucleic acids. If needed, the available sulfhydryls can be introduced by thiolation of the biorecognition molecule before coupling. Alternatively, a sulfhydryl-containing, amphiphilic CD polymer is coupled to any maleimide derivative of protein, ligand, nucleic acid or biotin, (e.g. biotin-maleimide) or iodoacetyl derivatives such as N-iodoacetyl-N'-biotinylhexylenediamine.

C. Maleimido-Biocleavable CDM Carriers and Iodo-Biocleavable CDM Carriers.

The maleimido-biocleavable CDM carriers, of this invention are suitable for coupling to native or introduced sulfhydryls on the desired biorecognition molecule.

A maleimido group is added to an amphiphilic amino-CD polymer suitably prepared as described previously, by coupling a suitable hetero-bifunctional coupling agent to the available amino group. The hetero-bifunctional coupling agent consists of a suitable spacer with a maleimide group at one end and an NHS ester at the other end. Examples are previously described and include MBS, SMCC, SMPB, SPDP, among others. The reaction is carried out so that the NHS ester couples to the available amino group on the CD polymer, leaving the maleimide group free for subsequent coupling to an available sulfhydryl on a biorecognition molecule.

Under appropriate conditions, amphipilic Iodo-Cyclodextrin (Iodo-CD) polymer carriers can be prepared for coupling to sulfhydryl groups. For instance, NHS esters of iodoacids can be coupled to the amino-CD polymers. Suitable iodoacids for use in this invention are iodopropionic acid, iodobutyric acid, iodohexanoic acid, iodohippuric acid, 3-iodotyrosine, among others. Before coupling to the amphiphilic amino-CD polymer, the appropriate Iodo-NHS ester is prepared by known methods. For instance, equimolar amounts of iodopropionic acid and N-hydroxysuccinimide are mixed, with suitable carbodiimide, in anhydrous dioxane at RT for 1–2 Hrs, the precipitate removed by filtration, and the NHS iodopropionic acid ester is collected in the filtrate. The NHS iodopropionic acid ester is then coupled to the amphiphilic amino-CD polymer.

PREPARATION VI

Biotinylated Biocleavable CDM Carriers

Biotinylated CD micelle carriers can be produced by a variety of known biotinylation methods suitably modified for use with CD's. For instance, combining an amphiphic amino-CD polymer derivative with a known N-hydroxysuccinimide derivative of biotin in appropriate buffer such as 0.1 M phosphate, pH 8.0, reacting for up to 1 hour at room temperature. Examples of biotin derivatives that can be used are, biotin-N-hydroxysuccinimide, biotinamidocaproate N-hydroxysuccinimide ester or sulfosuccinimidyl 2-(biotinamino)ethyl-1,3'-dithiopropionate, among others.

Through the use of suitable protection and deprotection schemes, as needed, any amphiphilic CD polymer of the instant invention can be coupled to biotin or a suitable derivative thereof, through any suitable coupling group. For instance, biocytin can be coupled through an available amino group to any NHS-CD label described herein.

PREPARATION VII

Amylose Micelle Carriers

The helical segments of amyloses, can be suitably polymerized, derivatized and/or capped to produce an amphiphilic molecule that is used to produce a micelle carrier for active agents. Also, they can be used in a biocleavable micelle carrier for active agents wherein suitable biocleavable linkages or coupling groups are included. Yet another composition includes the use of amylose derivatives as block polymers for copolymerization with other polymers to produce amphiphilic diblocks and triblocks.

Suitably, these amylose polymers have the necessary properties to form an inclusion complex with a drug or other active agent and can be used to produce new and useful compositions. Preferred substances are any amphiphilic polymers that contain helical segments of amyloses. Especially useful are helical amylose molecules of more than 5 and less than 120 glucose units, that favor formation of rigid linear helixes.

In one preferred embodiment, the amylose segments are first derivatized before being used in a micelle to entrap a drug. For instance, some or all of the available hydroxyl groups are suitably thiolated by various methods described herein for thiolating cyclodextrins, to provide sulfhydryl groups along the "edges" of the amylose chain. This can be done by first adding thiosulfate groups by coupling 1,3-propane sultone or 1,4-butane sultone directly to the hydroxyl groups on the amylose. The thiosulfate esters are subsequently reduced to sulfhydryls with dithiothreitol.

In another preferred embodiment, the amylose segments are derivatized by various methods described herein for cyclodextrins, to provide amino groups along the "edges" of the amylose chain.

Another preferred embodiment has incorporated cross-links that contain biocleavable linkages between the sulfhydryl or amino groups as described previously.

Helical amylose polymers can be targeted by coupling them to biorecognition molecules such as proteins, polypeptides, lipids, lipoproteins, nucleic acids, surfactants, virus coat proteins, and organic molecules. They can include intermediate substances of acrylamides (HPMA), PEG, nylons, polystyrenes, resins, metals and celluloses, and their combinations.

Amylose Blocks.

Amylose blocks (AM-Block) are compositions that provide for the incorporation of amylose derivatives into micelle-forming amphiphilic molecules through copolymerization with other polymer blocks. The AM-blocks can be primarily hydrophilic to produce micelles with the amylose moieties in the hydrophilic shell. Or, the AM-blocks can be primarily hydrophobic to produce micelles with the amylose moieties in the hydrophobic core.

To produce micelle-forming diblock or triblock amphiphilic molecules using AM-blocks, the amylose can be suitably derivatized and/or protected as previously described or referenced for cyclodextrins. The AM-blocks also have available suitable reactive groups that can copolymerize with other block polymers, using suitably modified methods described and referenced by G. S. Kwon, Ind.: Critical Reviews in Therapeutic drug Carrier Systems, 15(5):481–512 (1998).

For example, an amylose derivative is prepared and made hydrophobic by adding alkyl or aromatic groups (i.e. methylation, ethylation, or benzylation) The amylose segments are derivatized by various methods described herein for cyclodextrins, to provide hydrophobic groups along the "edges" of the amylose chain. The amylose also has available an N carboxyanhydride (NCA) group coupled through a suitable spacer.

One form of AM-block would be: Methylated-AM-poly (aspartate)$_N$-NCA

This AM-block (where N=1–10) can then be copolymerized with suitable blocks of alpha-Methyl-omega-Amino-Poly(ethylene oxide) (PEO) in suitable solvent (CHCl$_3$:DMF) to produce a micelle-forming diblock amphiphilic molecule. The resulting diblock is: AM-block-PEO. With suitable modifications PEG can be used in place of PEO. Also, triblocks such as PEO-block-CD-block-PEO can be prepared.

While the invention has been described with reference to certain specific embodiments, it is understood that changes may be made by one skilled in the art and it would not thereby depart from the spirt and scope of the invention, which is limited only by the claims appended hereto.

What is claimed is:

1. A controlled release pharmaceutical micelle composition comprising;
   a) a biocleavable micelle containing an active agent selected from the group consisting of prodrugs, anticancer drugs, antineoplastic drugs, antifungal drugs, antibacterial drugs, antiviral drugs, cardiac drugs, neurological drugs, alkaloids, antibiotics, bioactive pepticles, steroids, steroid hormones, polypeptide hormones, interferons, interleukins, narcotics, prostaglandins, purines, pyriinidines, anti-protozoan drugs, barbiturates, photosensitizer substances and anti-parasitic drugs, and;
   b) wherein the micelle contains amphiphilic cyclodextrin molecules selected from the group consisting of alpha-cyclodextrins, beta-cyclodextrmns, gamma-cyclodextrins and their combinations, carboxymethyl cyclodextrins, glucosyl cyclodextrins, maltosyl cyclodextrins, hydroxypropyl cyclodextrins, 2-hydroxypropyl cyclodextrins, 2,3-dihydroxypropyl cyclodextrmns, sulfobutylether cyclodextrins, ethylated cyclodextrins, methylated cyclodextrins, oxidized cydodextrins, sulfonylated cydodextrins, dialdehyde cyclodextrins, amino cyclodextrins, iodinated cyclodextrmns, sulfhydryl cyclodextrins, thiosulfate cyclodextrins, carboxylic acid cyclodextrins, cyclodextrins derivatized through amidation, esterification, acylation, N-alkylation, allylation, ethynylation, oxidation, halogenation, hydrolysis, reactions with anhydrides, hydrazines, other amines, including cyclodextrins derivatized to form acetals, aldehydes, amides, imides, carbonyls, esters, isopropylidenes, nitrenes, osazones, oximes, propargyls, sulfonates, sulfonyls, sulfonamides, nitrates, carbonates, metal salts, hydrazones, glycosones, mercaptals, and combinations of these, cyclodextrin dimers, cyclodextrin trimers, and cyclodextrin polymers, and;

c) wherein hydrophilic head groups of said amphiphilic cyclodextrin molecules are covalently cross-linked through a biocleavable linkage selected from the group consisting of a disulfide linkage, a protected disulfide linkage, an ester linkage, an ortho ester linkage, a biocleavable polypeptide, an aromatic azo linkage, an aldehyde bond, a maleimide bond, an NHS bond and a hydrazone linkage, to form a stabilized micelle that has completely entrapped the active agent and wherein the cross-linking provides the function of controlled release.

2. The composition of claim 1 further comprising a biorecognition molecule coupled to the pharmaceutical micelle composition.

3. The composition of claim 1 wherein the active agent is selected from the group consisting of amphotericins, camptothecins, ganciclovir, furosemide, indometbacin, chiorpromazine, methotrexate, penicillins, anthracyclines, teramycins, tetracyclines, chiorotetracyclines, clomocyclines, cyclosporins, butoconazole, charteusin, elsamicin, ellipticines, guamecyclines, macrolides, filipins, fungichromins, nystatins, 5'-fluorouracil, 5'-fluoro-2'-deoxyuridine, allopurinol, taxanes and wortmannin.

4. The composition of claim 1 wherein the amphiphilic cyclodextrin molecules are selected from the group consisting of combinations of an alpha CD with a beta CD, an alpha CD with a gamma CD, a beta CD with a gamma CD and polymers with various ratios of alpha, beta and gamma cyclodextrins.

5. The composition of claim 1 wherein the amphiphilic cyclodextrin molecules are selected from the group consisting of CD block copolymers.

6. A controlled release pharmaceutical micelle composition comprising;
   a) a biocleavable micelle containing a nucleic acid, and;
   b) wherein the micelle contains amphiphilic cyclodextrin molecules selected from the group consisting of alpha-cyclodextrins, beta-cyclodextrins, gamma-cyclodextrins and their combinations, carboxymethyl cyclodextrins, glucosyl cyclodextrins, maltosyl cyclodextrins, hydroxypropyl cyclodextrins, 2-hydroxypropyl cyclodexirins, 2,3-dihydroxypropyl cyclodextrins, sulfobutylether cyclodextrins, ethylated cyclodextrins, methylated cyclodextrins, oxidized cyclodextrins, sulfonylated cyclodextrins, dialdehyde cyclodextrins, amino cyclodextrins, iodinated cyclodextrins, sulfhydryl cydodextrins, thiosulfate cyclodextrins, carboxylic acid cyclodextrins, cyclodextrins derivatized through amidation, esterification, acylation, N-alkylation, allylation, ethynylation, oxidation, halogenation, hydrolysis, reactions with anhydrides, hydrazines, other amines, including cyclodextrins derivatized to form acetals, aldehydes, amides, imides, carbonyls, esters, isopropylidenes, nitrenes, osazones, oximes, propargyls, sulfonates, sulfonyls, sulfonamides, nitrates, carbonates, metal salts, hydrazones, glycosones, mercaprals, and combinations of these, cyclodextrin dimers, cyclodextrin trimers, and cyclodextrin polymers, and;
   c) wherein hydrophilic head groups of said amphiphilic cyclodextrin molecules are covalently cross-linked through a biocleavable linkage selected from the group consisting of a disulfide linkage, a protected disulfide linkage, an ester linkage, an ortho ester linkage, a biocleavable polypeptide, an aromatic azo linkage, an aldehyde bond, a maleimide bond, an NHS bond and a hydrazone linkage, to form a stabilized micelle that has completely entrapped the nucleic acid and wherein the cross-linking provides the function of controlled release.

7. The composition of claim 6 further comprising a biorecognition molecule coupled to the pharmaceutical micelle composition.

8. A controlled release pharmaceutical micelle composition comprising;
   a) a biocleavable micelle containing an active agent selected from the group consisting of prodrugs, anti-cancer drugs, antineoplastic drugs, antifungal drugs, antibacterial drugs, antiviral drugs, cardiac drugs, neurological drugs, alkaloids, antibiotics, bioactive peptides, steroids, steroid hormones, polypeptide hormones, interferons, interleukins, narcotics, prostaglandins, purines, pyrimidines, anti-protozoan drugs, barbiturates, photosensitizer substances and anti-parasitic drugs, and;
   b) wherein the micelle contains amphiphilic molecules, and;
   c) wherein hydrophilic head groups of said amphiphilic molecules are covalently cross-linked through a biocleavable linkage selected from the group consisting of a disulfide linkage, a protected disulfide linkage, an ester linkage, an ortho ester linkage, a biocleavable polypeptide, an aromatic azo linkage, an aldehyde bond, a maleimide bond, an NHS bond and a hydrazone linkage, to form a stabilized micelle that has completely entrapped the active agent and wherein the cross-linking provides the function of controlled release.

9. The composition of claim 8 further comprising a biorecognition molecule coupled to the pharmaceutical micelle composition.

10. The composition of claim 8 wherein the active agent is selected from the group consisting of amphotericins, camptothecins, ganciclovir, furosemide, indomethacin, chiorpromazine, methotrexate, penicillins, anthracylines, teramycins, tetracyclines, chlorotetracyclines, clomocyclines, cyclosporins, butoconazole, charteusin, elsamicin, ellipticines, guamecyclines, macrolides, filipins, fungichromins, nystatins, 5'-fluorouracil, 5'-fluoro-2'-deoxyuridine, allopurinol, taxanes and wortmannin.

* * * * *